US008506952B2

(12) United States Patent
Minbiole et al.

(10) Patent No.: US 8,506,952 B2
(45) Date of Patent: Aug. 13, 2013

(54) PROBIOTIC COMPOSITIONS AND PROCESS THEREOF

(75) Inventors: Kevin P. C. Minbiole, Dayton, VA (US); Reid Harris, Harrisonburg, VA (US)

(73) Assignee: James Madison Innovations, Inc., Harrisonburg, VA (US)

( * ) Notice: Subject to any disclaimer, the term of this patent is extended or adjusted under 35 U.S.C. 154(b) by 59 days.

(21) Appl. No.: 12/829,520

(22) Filed: Jul. 2, 2010

(65) Prior Publication Data
US 2011/0002891 A1  Jan. 6, 2011

Related U.S. Application Data

(60) Provisional application No. 61/222,964, filed on Jul. 3, 2009.

(51) Int. Cl.
*A01N 63/00* (2006.01)

(52) U.S. Cl.
USPC .......................................... 424/93.4; 424/93.1

(58) Field of Classification Search
USPC ................................................ 424/93.4, 93.1
See application file for complete search history.

(56) References Cited

U.S. PATENT DOCUMENTS

| 4,900,348 | A | 2/1990 | Hoitink |
| 5,081,225 | A | 1/1992 | O'Sullivan et al. |
| 5,428,175 | A | 6/1995 | Hoshino et al. |
| 6,244,346 | B1 | 6/2001 | Perriello |
| 6,245,235 | B1 | 6/2001 | Perriello |
| 6,461,607 | B1 | 10/2002 | Farmer |
| 6,531,126 | B2 | 3/2003 | Farmer |
| 6,645,506 | B1 | 11/2003 | Farmer |
| 6,716,435 | B1 | 4/2004 | Farmer et al. |
| 6,723,326 | B1 | 4/2004 | Farmer |
| 6,733,751 | B2 | 5/2004 | Farmer |
| 6,811,786 | B1 | 11/2004 | Farmer et al. |
| 6,849,256 | B1 | 2/2005 | Farmer |
| 6,905,692 | B2 | 6/2005 | Farmer |
| 6,926,831 | B2 | 8/2005 | Matsumura et al. |
| 6,962,697 | B2 | 11/2005 | Cavaliere Vesely et al. |
| 7,025,974 | B2 | 4/2006 | Farmer et al. |
| 7,048,950 | B2 | 5/2006 | Farmer |
| 7,052,688 | B2 | 5/2006 | De Simone |
| 7,060,465 | B2 | 6/2006 | Xu et al. |
| 7,232,571 | B2 | 6/2007 | Farmer et al. |
| 7,244,607 | B2 | 7/2007 | Martin et al. |
| 7,371,407 | B2 | 5/2008 | Farmer |
| 7,374,753 | B1 | 5/2008 | Farmer et al. |
| 7,507,402 | B1 | 3/2009 | Farmer et al. |
| 7,541,042 | B2 | 6/2009 | Farmer |
| 7,544,363 | B2 | 6/2009 | Farmer |
| 7,651,680 | B2 | 1/2010 | Breton et al. |
| 7,700,093 | B2 | 4/2010 | Farmer et al. |
| 7,708,988 | B2 | 5/2010 | Farmer |
| 7,713,726 | B2 | 5/2010 | Farmer |
| 7,807,185 | B2 | 10/2010 | Farmer |
| 8,097,247 | B2 | 1/2012 | Farmer |

| 2003/0072829 | A1 | 4/2003 | Austin, Jr. |
| 2004/0243076 | A1 | 12/2004 | Husmark et al. |
| 2005/0201996 | A1 | 9/2005 | Conway et al. |
| 2005/0271758 | A1 | 12/2005 | Farmer |
| 2009/0186057 | A1* | 7/2009 | Farmer et al. ................. 424/404 |

FOREIGN PATENT DOCUMENTS

| JP | 06-253864 | 9/1994 |
| JP | 06-341069 | 12/1994 |
| JP | 07-227290 | 8/1995 |
| JP | 01-139612 | 5/1998 |
| JP | 10-113169 | 6/1998 |
| JP | 11-152687 | 6/1999 |
| JP | 05-126375 | 5/2005 |
| KR | 1020070088150 | 8/2007 |

OTHER PUBLICATIONS

Lauer et al. (Diversity of cutaneous bacteria with antifungal activity isolated from female four-toed salamanders. The ISME Journal. Published online Dec. 13, 2007).*
PCT/US2010/040898, International Search Report.
Ellis DH. Diagnosis ot onychomycosis made simple. J Am Acad Dermatol 1999; 40:S3-8.
Fostel J, et al., Emerging novel antifungal agents. Drug Discov Tod 2000;5:25-32.
Sanders M. Probiotics: Considerations for Human Health. Nutrition Reviews 2003: 91-99.
Isolaurie, et al., Probiotics in the Management of Atopic Eczema. Clinical and Experimental Allergy. 2000. 30:1604-1610.

(Continued)

*Primary Examiner* — Karen Cochrane Carlson
*Assistant Examiner* — Natalie Moss
(74) *Attorney, Agent, or Firm* — Edgar G. Rodriguez (57) ABSTRACT

Probiotic composition(s) and/or process(es) thereof. Processes may include applying *Janthinobacterium*, for example *Janthinobacterium lividum*, over a host and/or host area(s) to minimize microbe(s) and/or maximize therapeutic effects. A process to minimize a microbe may include applying to skin a composition including isolated *Janthinobacterium lividum* and a pharmaceutically acceptable carrier. Probiotic composition(s) and/or process(es) thereof may include relatively heat tolerant *Janthinobacterium lividum* which may produce metabolites, for example violacein up to approximately 29° C. Probiotic composition(s) and/or process(es) thereof may include *Janthinobacterium lividum* between approximately $25 \times 10^6$ and $6.4 \times 10^7$ cells. Probiotic composition(s) and/or process(es) thereof may include *Janthinobacterium lividum* which has and/or produces between approximately 18 μM and 129 μM of violacein. Probiotic composition(s) and/or process(es) thereof may include a stimulant to maximize metabolites. A process to minimize a microbe may include removing a portion of resident microbes with a sanitizer. *Janthinobacterium lividum* may be in lysed form.

16 Claims, 8 Drawing Sheets

(56) References Cited

OTHER PUBLICATIONS

Borneman J, et al., PCR Primers That Amplify Fungal rRNA Genes from Environmental Samples. Applied and Environmental Microbiology. 2000. 4356-4360.

Lauer, A. et al., Common Cutaneous Bacteria from the Eastern Red-Backed Salamander Can Inhibit Pathogenic Fungi. Copeia. 2007. 3:630-640.

Gueniche, A. et al., *Biffidobacterium longum* Lysate, a New Ingredient for Reactive Skin. Experimental Dermatology, vol. 19, issue 8 (Aug. 2010), p. e1-e8.

Becker M, et al., The bacterially-produced metabolite violacein is associated with survival in amphibians . . . Applied Environmental Microbiology. Nov. 2009, pp. 6635-6638.

Ouwehand A.C., et al., Probiotics of the skin: a new area of potential application? Lett Appl Microbiol 2003;36:327-31.

Grice, E. A., et al., A diversity profile of the human skin microbiota. Genome Research 2008. 18: 1043-1050.

Grice, E. A., et al., Topographical and Temporal Diversity of the Human Skin Microbiome. Science, 2009, 324, 5931, 1190-1192.

Kruttman, J. Pre- and probiotics for human skin. Journal of Dermatological Science. 2009, 54, 1-5.

Koburger J. A, et al., Isolation of *Chromobacterium* spp. from Foods, Soil, and Water, Applied and Environmental Microbiology, 1982, 1463-1465.

Cherif A, et al, *Pseudomonas* isolates have in vitro antagonistic activity against . . . Journal de Mycologie Medicale. 2009. 19, 178-184.

Pantanella F, et al., Violacein and biofilm production in *Janthinobacterium lividum*. Journal of Applied Microbiology. 2009. 1364-5072.

Effendy I, et al., Epidemiology and clinical classification of onychomycosis. J Eur Acad Dermatol Venereol 2005. 19:8-12.

Gill D, et al., A review of epidemiology of tinea unguium in the community. Austral J Dermatol 1999; 40:6-13.

Harris RN, et al., Skin microbes on frogs prevent morbidity and mortality caused by a lethal skin fungus, The ISME J., 37(7):818-27, Epub. Mar. 26, 2009.

Brucker RM, et al., Amphibian chemical defense: . . . , J. Chem. Ecol., Nov; 34(11):1422-9, 2008.

Yoskitoshi Nakamura, et al., Production of anitbacterial violet oigment by Phychrotropic bacterium RT012 strain, Biotech. and processes eng., 8:37-40, 2003.

Akira Shirata, et. al., Isolation of bacteria producting bluish-purple pigment and use for dyeing, LARQ, 34, 131-140, 2000.

PCT/US2010/040898, International Search Report, 2010.

* cited by examiner

| Treatment | Day | Shortest average linear distance from line(mm) | Shortest Average Linear distance from J.lividum(mm) |
|---|---|---|---|
| 2a | 9 | 6.41 | 2.32 |
| 2b | 9 | 10.39 | 6.68 |
| 2ctrl | 9 | 3.94 | n/a |
| 3a | 9 | 12.04 | 9.16 |
| 3b | 9 | 7.81 | 3.64 |
| 3ctrl | 9 | 3.06 | n/a |
| 4a | 9 | 10.16 | 5.44 |
| 4b | 9 | 14.28 | 9.31 |
| 4ctrl | 9 | 8.94 | n/a |
| 2a | 14 | 5.78 | 1.64 |
| 2b | 14 | 10.19 | 6.79 |
| 2ctrl | 14 | 3.94 | n/a |
| 3a | 14 | 11.85 | 8.75 |
| 3b | 14 | 6.00 | 3.34 |
| 3ctrl | 14 | 0.56 | n/a |
| 4a | 14 | 6.85 | 1.85 |
| 4b | 14 | 14.30 | 9.56 |
| 4ctrl | 14 | 4.11 | n/a |

PROBIOTIC COMPOSITIONS AND PROCESS THEREOF

The present application claims priority under 35 U.S.C. 119 to U.S. Provisional Patent Application No. 61/222,964 (filed on Jul. 3, 2009) which is hereby incorporated by reference in its entirety.

The subject matter of the present application was made with government support from the National Science Foundation under grant number 0640373. The government may have rights to the subject matter of the present application.

BACKGROUND

Embodiments relate to probiotic composition(s) and/or process(es) thereof. Some embodiments relate to applying *Janthinobacterium*, for example *Janthinobacterium lividum*, over a host and/or host area(s) to minimize microbe(s) and/or maximize therapeutic effects.

Infections may be a problem for a wide array of hosts. For example, there are a variety of infections, such as bacterial, viral and/or fungal infections, that affects a relatively large number of the human population. Dermatophytoses are common cutaneous infections caused by fungi such as *Tricophyton*, *Microsporum* and/or or *Epidermophyton* species. *Tricophyton rubrum* is responsible for approximately 46% to 72% of cutaneous and nail mycoses worldwide. Onychomycosis, a common and persistent fungal infection, is diagnosed in two to eight percent of the global population. The disease may cause disfigurement of nails and/or pain.

Treatments for dermatophytoses may include antifungal topical products (e.g., terbinafine, itraconazole, miconazole, etc.) and/or systemic therapy. However, some of these treatments may take many months to address an infection and/or require a relatively large number of applications. Furthermore, the growing problem of antibiotic resistance and the toxicity of relatively long term treatments has formed a need for an alternative treatment in human populations. Probiotics have been utilized for their role in the protection of the digestive tract. More recently, probiotics have been explored for their dermatological applications, although none have included *Janthinobacterium*, for example species and/or strains thereof such as *Janthinobacterium lividum*, to minimize a microbe and/or maximize a maximize therapeutic effect.

There are also a variety of infections that affects a relatively large amount of other populations. For example, an emerging infectious disease, chytridiomycosis, is a major factor responsible for extinction of amphibian species. One-third of amphibian species are threatened with extinction. Caused by the chytrid species *Batrachochytrium dendrohatidis*, this skin disease may be linked to population declines and extinctions of over 200 amphibian species in areas unaffected by habitat loss. Thus, there is a need for composition(s) and/or methods thereof which may address a variety of infections and/or be relatively clinically safe across a plurality of populations.

*Janthinobacterium lividum* may not be present at hosts and/or host area(s), and/or may not be present, produce and/or include metabolites in adequate amounts to provide a therapeutic effect. Furthermore, *Janthinobacterium* is a relatively heat intolerant water-borne gram negative bacterium, and may not produce and/or include metabolites, such as violacein, at relatively high temperatures. However, normal skin temperatures of a human may be between approximately 27° C. (e.g., foot temperature) and 36° C. (e.g., abdomen). Even in the case where skin temperature is lower than normal temperature, for example in colder weather or skin of a human diabetic, *Janthinobacterium lividum* may not be present at hosts and/or host area(s) in adequate amounts to provide a therapeutic effect, for example due to inadequate cell density, lack of a stimulant to maximize metabolite production and/or competition from resident flora.

SUMMARY

Embodiments relate to probiotic composition(s) and/or process(es) thereof. According to embodiments, probiotic composition(s) may be applied over a wide array of host and/or host area(s), for example skin. In embodiments, probiotic composition(s) may minimize a microbe and/or include maximized therapeutic effects. In embodiments, microbe(s) which may be minimized may include bacteria, yeast, fungus, virus, and the like. In embodiments, for example, fungus which may be minimized may include *Tricophyton rubrum*.

According to embodiments, process(es) to minimize a microbe may include applying *Janthinobacterium* over a host and/or host area(s). In embodiments, process(es) to minimize a microbe may include applying a composition including isolated *Janthinobacterium lividum* to a host and/or host area(s). In embodiments, *Janthinobacterium lividum* may be isolated from a salamander, for example *Hemidactylium scutatum*. In embodiments, a host and/or host area(s) may include skin, such as human foot skin.

According to embodiments, process(es) to minimize a microbe may include applying *Janthinobacterium* and a pharmaceutically acceptable carrier over a host and/or host area(s). In embodiments, process(es) to minimize growth of a microbe may include applying a composition having isolated *Janthinobacterium lividum* and a pharmaceutically acceptable carrier over a host and/or host area(s). In embodiments, a pharmaceutically acceptable carrier may include an emulsion, paste, cream, lotion, gel, jelly, ointment, oil, aerosol, powder and/or solvent, and the like. In embodiments, a solvent may include water, for example deionized water.

According to embodiments, process(es) to minimize a microbe may include applying *Janthinobacterium* having metabolites over a host and/or host area(s). In embodiments, process(es) to minimize a microbe may include applying *Janthinobacterium* which may produce metabolites over a host and/or host area(s). In embodiments, process(es) to minimize growth of a microbe may include applying a composition having isolated *Janthinobacterium lividum* which may produce metabolites, for example violacein, over a host and/or host area(s). In embodiments, process(es) to minimize a microbe may include applying a composition having isolated *Janthinobacterium lividum* which may include and/or produce metabolites at relatively high temperatures, for example violacein at relatively high temperatures, over a host and/or host area(s). In embodiments, isolated *Janthinobacterium lividum* may include and/or produce violacein up to approximately 29° C.

According to embodiments, process(es) to minimize a microbe may include application of *Janthinobacterium* having metabolites where *Janthinobacterium* may be in a lysed form, for example a composition including *Janthinobacterium lividum* in lysed form with violacein. In embodiments, process(es) to minimize a microbe may include collecting metabolites of *Janthinobacterium*, for example of isolated *Janthinobacterium lividum*, and applying a composition including collected metabolites. In embodiments, collecting metabolites may include collection from supernatant. In embodiments, collecting metabolites may include lysing isolated *Janthinobacterium lividum* and employing part and/or substantially all of a lysate.

According to embodiments, process(es) to minimize a microbe may include applying *Janthinobacterium* to host area(s) in an effective amount to minimize a microbe. In embodiments, an effective amount may include introduced and/or augmented cell density of *Janthinobacterium lividum* to minimize a microbe. In embodiments, for example, an effective amount may include a density of between approximately $25\times10^6$ and $6.4\times10^7$ *Janthinobacterium lividum* cells. In embodiments, process(es) to minimize a microbe may include applying *Janthinobacterium* and a pharmaceutically acceptable carrier to host and/or host area(s) in an effective amount to minimize growth of a microbe. In embodiments, for example, an effective amount may include between approximately $25\times10^6$ and $6.4\times10^7$ *Janthinobacterium lividum* cells per ml of pharmaceutically acceptable carrier. In embodiments, an effective amount may include selected metabolite concentration, for example between approximately 18 μM and 129 μM violacein.

According to embodiments, process(es) to minimize a microbe may include applying *Janthinobacterium* and a stimulant over a host and/or host area(s), and/or metabolites manufactured using a stimulant. In embodiments, a stimulant may include quorum sensing molecules, for example N-(3-oxyooctanoyl)-homoserine lactone. In embodiments, a stimulant may include tryptophan, which may maximize the production and/or amount of violacein.

According to embodiments, process(es) to minimize a microbe may include removing a part and/or substantially all resident microbe(s) from a host and/or host area(s). In embodiments, process(es) to minimize a microbe may include removing substantially all resident microbe(s) employing a sanitizer, for example prior to applying *Janthinobacterium lividum* over a host and/or host area(s). In embodiments, process(es) to minimize growth of a microbe may include removing substantially all resident microbes, for example with a sanitizer including hydrogen peroxide, and applying *Janthinobacterium lividum* and/or metabolites thereof to a host.

DRAWINGS

Example FIG. 1 illustrates the effect of treatment on host survival in accordance with embodiments.

Example FIG. 2 illustrates the effect of treatment on proportional growth of a host in accordance with embodiments.

Example FIG. 3 illustrates the effect of treatment on the mean number of zoospore equivalents of *B. dendrobatidis* of frogs in accordance with embodiments.

Example FIG. 4 illustrates the effect of treatment on violacein concentration on host skin in accordance with embodiments.

Example FIG. 5 is a table illustrating measured linear distances between *Tricophyton rubrum* (*T. rubrum*) and the dividing lines or *Janthinobacterium lividum* on dual culture challenge assays in accordance with embodiments.

Example FIG. 6 illustrates treatment 1a taken fourteen days into a dual culture challenge assay in accordance with embodiments.

Example FIG. 7 illustrates treatment 1ctrl taken fourteen days into a dual culture challenge assay in accordance with embodiments.

Example FIG. 8 illustrates treatment 2b taken fourteen days into a dual culture challenge assay in accordance with embodiments Example FIG. 9 illustrates treatment 2ctrl taken fourteen days a dual culture challenge assay in accordance with embodiments.

Example FIG. 10 illustrates treatment 3a taken fourteen days into a dual culture challenge assay in accordance with embodiments.

Example FIG. 11 illustrates treatment 3ctrl taken fourteen days into a dual culture challenge assay in accordance with embodiments.

Example FIG. 12 illustrates treatment 4b taken fourteen days into a dual culture challenge assay in accordance with embodiments.

Example FIG. 13 illustrates treatment 4ctrl taken fourteen days into a dual culture challenge assay in accordance with embodiments.

Example FIG. 14 illustrates an increase of violacein peak height as L-Tryp concentrations increase in accordance with embodiments.

Example FIG. 15 illustrates an increase in violacein concentration as L-Tryp concentrations increases in accordance with embodiments.

DESCRIPTION

Embodiments relate to probiotic composition(s) and/or process(es) thereof. A probiotic may relate to microorganisms (e.g., bacteria, yeast, fungus and/or virus) which may form a portion of host flora, for example transient flora, and/or which may confer a therapeutic benefit to a host, for example when administered in adequate amounts. A probiotic composition, for example including microorganism(s) and/or metabolite(s) thereof, may be relatively clinically safe (i.e., substantially non-pathogenic). According to embodiments, probiotic composition(s) and/or process(es) thereof may minimize microbe(s) and/or maximize therapeutic effects, for example in the treatment of skin infections, diseases, ailments, and the like.

According to embodiments, composition(s) and/or process(es) may include *Janthinobacterium* and/or metabolites thereof, which when applied over a host in adequate amounts may confer a relatively clinically safe health benefit. In embodiments, such health benefits may include minimizing, treating and/or managing infections caused by microbe(s) (e.g., pathogens), for example bacterial, yeast, fungal and/or viral infections, and the like.

According to embodiments, probiotic composition(s) may be applied over a wide array of hosts. In embodiments, a host may include a human host, an amphibian host, for example frogs and/or salamanders, and the like. In embodiments, for example where *Janthinobacterium* may be part of host resident flora, *Janthinobacterium* species such as *Janthinobacterium lividum*, and/or strains thereof, may be employed to augment cell density and/or to provide a substantial therapeutic effect. In embodiments, species of *Janthinobacterium* and/or strains thereof, for example relatively heat tolerant strains of *Janthinobacterium lividum* and/or strains isolated from the salamander *Hemidactylium scutatum*, may be employed in adequate amounts to introduce and/or augment specific metabolites which may not be present at hosts and/or which may not be present in adequate amounts to provide a therapeutic effect.

According to embodiments, probiotic composition(s) may be applied over a wide array of host area(s). In embodiments, probiotic composition(s) including isolated *Janthinobacterium lividum* may be applied at internal areas of a host, for example a portion of a mouth, gastrointestinal tract, lungs and/or mucous membranes, and the like. In embodiments, probiotic composition(s) including isolated *Janthinobacterium lividum* may be applied at external areas of a host, for example skin, nails and/or hair, and the like. In embodiments, for example, skin may include human foot skin, abdomen skin and/or face skin, and the like.

According, to embodiments, for example where *Janthinobacterium* may form a part of host resident flora, *Janthinobacterium* species such as *Janthinobacterium lividum*, and/or strains thereof, may be employed to augment and/or introduce *Janthinobacterium* at host area(s) of interest. In embodiments, species of *Janthinobacterium* and/or strains thereof, for example relatively heat tolerant strains of *Janthinobacterium lividum* and/or strains isolated from the salamander *Hemidactylium scutatum*, may be employed in adequate amounts to introduce and/or augment metabolites which may not be present at hosts area(s) and/or which may not be present in adequate amounts to provide a therapeutic effect.

According to embodiments, process(es) including probiotic composition(s) having isolated *Janthinobacterium lividum* and/or metabolites thereof, for example violacein, may minimize a microbe and/or may include maximized therapeutic effects. In embodiments, microbe(s) which may be minimized may include bacteria, yeast, fungus and/or virus, and the like. Process(es) including probiotic composition(s) having isolated *Janthinobacterium lividum* and/or metabolites thereof may include antitumor, antibacterial, antileishmanial, antiviral, antitrypanosome and/or antifungal therapeutic effects.

According to embodiments, for example, maximized therapeutic effects may include minimizing, treating and/or managing fungus, such as *Tricophyton rubrum* and/or *Batrachochytrium dendrobatidis*. In embodiments maximized therapeutic effects may include minimizing, treating and/or managing infections, such as Tinea pedis (i.e., Athlete's foot) and/or Chytridiomycosis. Process(es) including probiotic composition(s) having isolated *Janthinobacterium lividum* and/or metabolites thereof may be useful in addressing parasitic diseases such as cutaneous leishmaniasis, and/or bacterial conditions such as methicillin-resistant staphylococcus aureus (MRSA) and/or acne.

According to embodiments, process(es) to minimize a microbe may include applying *Janthinobacterium* and a pharmaceutically acceptable carrier over a host and/or host area(s). In embodiments, a pharmaceutically acceptable carrier may include a capsule, bandaid, bandage, diaper, patch, tape, fibers, scaffold, and/or matrix, and the like. In embodiments, a pharmaceutically acceptable carrier may include an emulsion, paste, cream, lotion, gel, jelly, ointment, oil, aerosol, powder, whether organic, inorganic, synthetic and/or natural. In embodiments, a pharmaceutically acceptable carrier may include a solvent, for example water, which may include deionized water. In embodiments, a pharmaceutically acceptable carrier may include suitable diluents, preservatives, solubilizers, emulsifiers, adjuvants and/or bulking substances, and the like. Process(es) to minimize a microbe may include applying isolated *Janthinobacterium lividum* and a pharmaceutically acceptable carrier over host skin, for example human foot skin, in accordance with embodiments.

According to embodiments, process(es) to minimize a microbe may include applying *Janthinobacterium* having metabolites over a host and/or host area(s). In embodiments, process(es) to minimize a microbe may include applying *Janthinobacterium* which may produce metabolites over a host and/or host area(s). In embodiments, process(es) to minimize a microbe may include applying a composition having isolated *Janthinobacterium lividum* which may produce metabolites, for example violacein and/or indole-3-carboxaldehyde, over a host and/or host area(s). In embodiments, *Janthinobacterium* may be in a lysed form. In embodiments, for example, probiotic composition(s) may include *Janthinobacterium lividum* in lysed form together with a part and/or substantially all metabolites, for example substantially all violacein.

According to embodiments, process(es) to minimize a microbe may include collecting metabolites of *Janthinobacterium*, for example of isolated *Janthinobacterium lividum*, and applying a composition including collected metabolites over a host and/or host area(s). In embodiments, collecting metabolites may include incubating *Janthinobacterium*, for example *Janthinobacterium lividum*, centrifuging the culture and collecting the supernatant to capture metabolites thereof. In embodiments, additional process(es) may be performed to collect metabolites, for example separation process(es) such as gradient centrifugation, chromatography (e.g., liquid, affinity, etc.), and the like. In embodiments, *Janthinobacterium lividum* may be cultured and centrifuged a plurality of times, such that a desired quantity of supernatant and/or concentration of metabolite may be collected.

According to embodiments, collecting metabolites may include lysing *Janthinobacterium* and applying a part and/or substantially all of a lysed product over a host and/or host area(s). In embodiments, for example, isolated *Janthinobacterium lividum* may be lysed such that a lysate including metabolites may be employed. In embodiments, additional process(es) may be performed to collect metabolites, for example separation process(es) such as gradient centrifugation, chromatography (e.g., liquid, affinity, etc.), and the like. In embodiments, any suitable process may be employed to manufacture a lysed product, including ultrasound lysing, for example sonication, enzymatic lysing, for example using lysozyme, and the like.

According to embodiments, process(es) to minimize a microbe may include applying a composition having isolated *Janthinobacterium lividum*, which may include and/or produce metabolites at relatively high temperatures, over a host and/or host area(s). Resident *Janthinobacterium* may minimize or substantially cease metabolite production, and/or may be substantially or totally depleted, at relatively high temperatures. In embodiments, probiotic composition(s) including isolated *Janthinobacterium lividum* may be relatively heat tolerant and/or may produce metabolites such as violacein at relatively high temperatures, for example at approximately 29° C.

According to embodiments, process(es) may include applying *Janthinobacterium* to a host and/or host area(s) in an effective amount to minimize a microbe. In embodiments, an effective amount may include introduced and/or augmented cell density of *Janthinobacterium*, for example *Janthinobacterium lividum*, to minimize a microbe. In embodiments, for example, an effective amount may include a density between approximately $25 \times 10^6$ and $6.4 \times 10^7$ *Janthinobacterium lividum* cells. In embodiments, process(es) to minimize a microbe may include applying to a host and/or host area(s) *Janthinobacterium* and a pharmaceutically acceptable carrier in an effective amount to minimize growth of a microbe. In embodiments, for example, an effective amount may include $25 \times 10^6$ *Janthinobacterium lividum* cells per ml of pharmaceutically acceptable carrier, such as deionized water. In embodiments, for example, an effective amount may include $6.4 \times 10^7$ *Janthinobacterium lividum* cells per ml of pharmaceutically acceptable carrier, for example Provosoli medium. In embodiments, an effective amount may include selected metabolite concentration, for example above approximately 1.82 µM violacein and/or 69 µM indole-3-carboxaldehyde, including between approximately 18 µM and 129 µM violacein.

According to embodiments, process(es) to minimize a microbe may include applying a composition including *Janthinobacterium* and a stimulant over a host and/or host area(s), and/or applying a composition having metabolite(s) manufactured using a stimulant. In embodiments; a stimulant may include a composition which may stimulate metabolite production and/or increase an amount of metabolite(s). In embodiments, a stimulant may include quorum sensing molecules, for example N-(3-oxyooctanoyl)-homoserine lactone. In embodiments, a stimulant may include tryptophan, which may maximize the production and/or amount of violacein. In embodiments, for example, a relatively lower density of *Janthinobacterium lividum* cells may be employed to manufacture substantially the same and/or a relatively larger concentration of metabolite(s), for example of violacein.

According to embodiments, process(es) to minimize a microbe may include removing a part and/or substantially all resident microbe(s) from a host and/or host area(s). In embodiments, process(es) to minimize a microbe may include removal employing a sanitizer, for example prior to applying *Janthinobacterium lividum* over host area(s). In embodiments, a sanitizer may include any medium operable to remove portion of resident microbe(s). In embodiments, a medium may include heat, radiation, composition, and the like. In embodiments, process(es) to minimize growth of a microbe may include removing substantially all resident microbes, for example with a sanitizer including hydrogen peroxide, prior to applying *Janthinobacterium lividum* and/or metabolites thereof to host area(s).

1. Example *Janthinobacterium* Embodiments

A. Example Accessible *Janthinobacterium Lividum* Embodiment

U.S. Pat. No. 5,081,225 to O'Sullivan et al., herein incorporated by reference in its entirety, includes a process that may be performed to isolate *Janthinobacterium lividum* from stagnant water. The process involves plating soil extract onto agar plates and identifying colonies by gross inspection (e.g., dark purplish black color). Such a strain may be obtained from the American Type Culture Collection (A.T.C.C.), deposited under accession number 53,857. It is believed that *Janthinobacterium*, including *Janthinobacterium lividum*, is readily available and/or may be isolated.

B. Example Isolated *Janthinobacterium Lividum* And Metabolites Thereof Embodiment In embodiments, *Janthinobacterium* and/or species thereof, for example *Janthinobacterium lividum*, may be isolated from the salamander *Hemidactylium scutatum*, which is readily available at least at the George Washington National Forest, Rockingham Co., Va., USA. In embodiments, such a strain of *Janthinobacterium lividum* may produce and/or includes, at least, the metabolites violacein and/or indole-3-carboxaldehyde.

According to embodiments, isolation may be completed using the process described in Lauer et al. (Copea., 3: 630-640, 2007). In embodiments, for example, sterile swabs, including cotton swabs (e.g., cotton tipped applicators, Hardwood Prod. Comp. LLC, Guilford, Me.) may be drawn over skin, for example of the salamander *Hemidactylium scutatum*. In embodiments, the swab may then be streaked over R2A-agar (Becton Dickenson, Sparks,. Md.) for bacterial cultivation. In embodiments, single colonies may be isolated and streaked on fresh R2A-plates until pure colonies are obtained. In embodiments, for example, single colonies of *Janthinobacterium lividum* may be isolated by gross examination due to colony color, form, margin form, and/or elevation and the like.

In embodiments, substantially pure isolated *Janthinobacterium lividum* may be incubated for approximately 72 hours at room temperature in approximately 1% tryptone. In embodiments, *Janthinobacterium lividum* may be continuously stirred. In embodiments, the culture may be centrifuged at approximately 4500 rpm for approximately 10 minutes. The supernatant may be collected and/or discarded in accordance with embodiments. In embodiments, the resulting pellet may be resuspended, for example in sterile Provosoli medium. In embodiments, the resulting composition may be diluted to form a desired density and/or concentration, for example to form a concentration of approximately $26.25 \times 10^6$ cells per ml.

In embodiments, metabolite collection may be accomplished according to the process described in Brucker et al. (J. Chem. Ecol. 34:1422-1429, 2008). For example, supernatant may be frozen and subsequently thawed, and metabolites may be extracted ×4 with ⅓ volume of ethyl acetate. Combined organic layers may be dried over $Na_2SO_4$, filtered, and evaporated in vacuo. However, metabolite collection may include any suitable process to collect a portion and/or substantially all of the metabolites of *Janthinobacterium lividum* and/or specific metabolites thereof, for example using detergents, alkali, enzymatic degradation and/or sonication, and the like. In embodiments, for example, *Janthinobacterium lividum* may be sonicated employing a sonicating probe and/or bath, for example using the sonicator SonicMan™ (Matrical Bioscience). The sonicator enables, for example, bacterial lysis at power outputs, between 100 and 1150 watts (12 watts/pin for 96 well formats and 3 watts/pin for 384 well formats at 100% power) and configurable time intervals from 0.1 to 20 seconds.

C. Example Isolated Relatively Heat Tolerant *Janthinobacterium Lividum* Embodiment In embodiments, *Janthinobacterium* and/or strains thereof, for example relatively heat tolerant strains of *Janthinobacterium lividum*, may be isolated, for example from the salamander *Hemidactylium scutatum*. However, while embodiments may relate to *Janthinobacterium lividum* isolated from the salamander *Hemidactylium scutatum* it is believed that *Janthinobacterium lividum* isolated from other sources, for example other salamander species such as the Eastern red-backed salamander *Plethodon cinereus*, may be employed.

*Janthinobacterium lividum* may produce the purple metabolite violacein, such that the presence of violacein may be relatively easily detected by gross examination. According to embodiments, isolated *Janthinobacterium lividum* may be grown on approximately 1% tryptone, approximately 1% agar plates, at room temperature. In embodiments, a sterile inoculating loop may be used approximately every two days to inoculate a new plate approximately 1° C. higher than the previous one. Since *Janthinobacterium* is a relatively heat intolerant bacterium, *Janthinobacterium lividum* may not survive for more than a few days on the plate at 29° C.

According to embodiments, the process may be started at approximately 24° C. and upon reaching approximately 28° C., there may be an increase by approximately 0.1° C. upon each replating. In embodiments, the process may be run on approximately 1% tryptone broth instead of agar and the like to maximize *Janthinobacterium lividum* stabilization and/or metabolite production. In embodiments, violacein may be detected at approximately 29° C., at gross scales. It is believed that the process(es) may be maximized to isolate heat tolerant strains of *Janthinobacterium lividum* at and/or above approximately 29° C. in accordance with embodiments.

2. Example Process(es) Embodiments

A. *Janthinobacterium Lividum* Over Amphibian Host And/Or Host Area(s) Embodiment 1. Materials And Processes Embodiment Thirty-one *R. muscosa* juveniles were obtained from a laboratory colony, raised from field-collected eggs, at the University of California, Berkeley. Each frog was placed into its own autoclaved plastic container containing approximately 200 ml of Provosoli medium and was randomly assigned a position on metal racks in a temperature-controlled room set at 17° C. with a 12 h light cycle. Containers were cleaned with 10% bleach and autoclaved twice a week. Each frog was fed five crickets weekly. Animal care protocols were approved by the University of California, Berkeley's and James Madison University's Animal Care and Use Committee. We performed a replicated, randomized experiment with three groups of *R. muscosa*: (1) *Batrachochytrium dendrobatidis* (Bd), exposure to Bd zoospores; (2) bacteria, exposure to *Janthinobacterium lividum* and (3) Bacteria+Bd, exposure to both *Janthinobacterium lividum* and Bd zoospores. Eighteen frogs were used in this experiment with the sample size for each treatment group being six frogs, with each frog in a separate container. There was no difference in mass among the three treatment groups at the beginning of the experiment (analysis of variance (ANOVA): d.f.=2,15, F=0.943, P=0.411). A preliminary experiment with another 10 juvenile *R. muscosa* was conducted to obtain a growth rate under standard laboratory conditions. This estimate was used as a comparison for growth rates estimated from the 18 frogs in the three manipulated treatment groups. Three other juveniles were used to estimate the concentration of violacein on individuals that were not subjected to any experimental manipulations.

Individuals were treated with a 25 ml solution of 3% hydrogen peroxide for 45 s, although any desired time may be employed such as 30 s, and rinsed with sterile Provosoli medium before returning to new containers. This process minimizes the number of bacterial species on the skin, thereby minimizing community interactions between *Janthinobacterium lividum* and other cutaneous bacterial species. Therefore, we could standardize initial conditions on the frogs' skins and more readily attribute treatment effects to the presence or absence of *Janthinobacterium lividum*. After a period of 24 h, each frog in the Bacteria and the Bacteria+Bd treatments was inoculated with *Janthinobacterium lividum* in individual containers. The *Janthinobacterium lividum* strain used was obtained from the skin of the salamander *Hemidactylium scutatum* collected in the George Washington National Forest, Rockingham Co., Va., USA and a concentration of approximately $26.25 \times 10^6$ cells per ml suspension was used.

Frogs were placed in autoclaved 120 ml GladWare containers (Glad Products Co., Oakland, Calif., USA) with 15 ml of the bacterial solution for 30 min. During this time, frogs in the Bd treatment were exposed to medium alone. Individuals were then placed into sterile containers for 48 h to allow *Janthinobacterium lividum* to establish on the skin of the inoculated frogs. At this time, individuals in the Bd and the Bacteria+Bd treatments were exposed to Bd zoospores. This day was considered day 1 of the experiment. Immediately before the exposure, all frogs were weighed. Frogs were individually placed in 120 ml GladWare containers with 300 zoospores suspended in 15 ml of Provosoli medium for 24 h. Alternatively, frogs in the Bacteria treatment were exposed to medium alone. The Bd strain JEL 215 isolated from *R. muscosa* was used for exposure. Cultures of the isolate were maintained in 1% tryptone and transferred weekly. The zoospore solution used to inoculate the frogs was prepared by growing zoospores on plates containing 1% tryptone and 1% agar. After a period of approximately 72 h, the plates were flooded with, 6 ml of Provosoli medium. After 20 min, the remaining solution was removed by pipette. The zoospore concentration was determined by a hemacytometer and diluted to 20 zoospores per ml.

After Bd exposure and the initial weight measurement, frogs were weighed approximately every 2 weeks. Sampling for *Janthinobacterium lividum* and for Bd was completed on seven days later and approximately every 2 weeks after this date. After rinsing each individual in sterile Provosoli medium twice, frogs were swabbed 10 times on their ventral surface with a rayon swab (Medical Wire and Equipment, Corsham, Wiltshire, UK) on the dorsal surface of the abdomen, legs and feet to detect Bd presence and to estimate abundance. The same procedure was carried out to assay for the presence of *Janthinobacterium lividum*. Swabs were frozen at −20° C. until further processing occurred. Swabs from 22, 61 and 139 days after exposure to Bd were sent to Pisces Molecular (Boulder, Colo., USA) for DNA extraction and for an estimate of Bd abundance using TaqMan PCR. Swabs from days 5, 19, 47 and 139 were assayed for the presence of *Janthinobacterium lividum* using PCR.

DNA was extracted from the swabs using a Qiagen DNeasy Blood and Tissue kit (Germantown, Md., USA) with the manufacturer's protocol. DNA obtained from the swabs was amplified using the *Janthinobacterium lividum*-specific primers JlivF and JlivR. These primers were designed using the *Janthinobacterium lividum* strain SKVTC8 violacein pigment gene obtained from GenBank (accession no. EU732703.1). PCR reactions (35 ml) contained 0.2 mM of each primer, 0.2 mM dNTPs, 2.5 U Taq polymerase with 1× buffer (1.5 mM $MgCl_2$, 50 mM KCl, 10 mM Tris; Fisher Scientific, Pittsburg, Pa., USA). The amplification conditions were approximately as follows: 4 min at 94° C. followed by 35 cycles of 30 s at 94° C., 60 s at 60° C. and 2 min at 72° C. The amplification was completed with a final extension for 10 min at 72° C. DNA from a pure culture of *Janthinobacterium lividum*, which was the same strain used in the experiment, was extracted with a MoBio Microbial Ultra Clean DNA kit (Carlsbad, Calif., USA) and amplified along with extracted swabs to act as a positive control. The amplification products were separated by electrophoresis through 2% agarose and stained with ethidium bromide (5 μgml$^{-1}$). Presence or absence of a band around 500 bp was determined for each swab using ultraviolet light. On the 140th day of the experiment, frogs were euthanized with carbon dioxide. The concentration of violacein on the skin was determined according to the method of Brucker et al. Differences in means were tested with ANOVA unless data were not normally distributed, in which case a nonparametric Wilcoxon test was used. A repeated-measures ANOVA was used to test for differences in the number of zoospores over time as a function of treatment. One value for zoospore equivalents in the Bacteria treatment was an extreme outlier (Dixon's test: $r_{10}$=1.0, n=6, P=0.01) and was not considered in the analysis. Frequency differences were tested with Fisher's exact test, and survival differences were tested with a Mantel-Cox log-rank test.

2. Results Embodiment a. Application of *Janthinobacterium Lividum* To Uninfected Frogs

Placing frogs into a solution with *Janthinobacterium lividum* led to successful colonization of the skin. Primers specific to *Janthinobacterium lividum* indicated that all individuals in the experiment had *Janthinobacterium lividum* on their skins, whether or not they were exposed to a bath of this bacterial species. However, the metabolite produced by *Janthinobacterium lividum*, violacein, was found only on the frogs bathed in the *Janthinobacterium lividum* solution, whereas frogs not treated had no detectable violacein on their skins. This result suggests that bathing in *Janthinobacterium lividum* increased population densities to the point where the secondary metabolite violacein was produced.

b. Survival Embodiment

Figure 1:
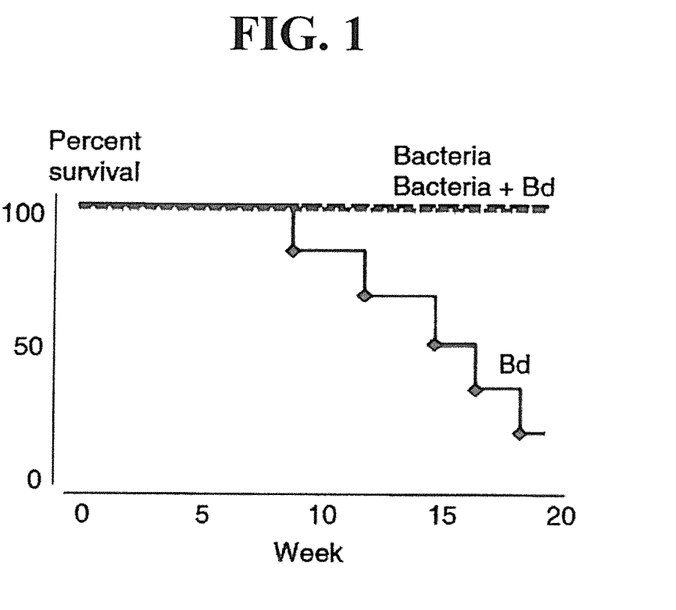

Referring to example FIG. 1, adding *Janthinobacterium lividum* to uninfected frogs prevented lethal effects of the disease. Five of six frogs in the Bd treatment died, and the sixth frog displayed symptoms of advanced-stage chytridiomycosis. No mortality occurred in the Bacteria and the Bacteria+Bd treatments (Mantel-Cox log-rank test: d.f.=2, $x^2$=15.877, P=0.0004).

c. Change In Weight Embodiment

Figure 2:
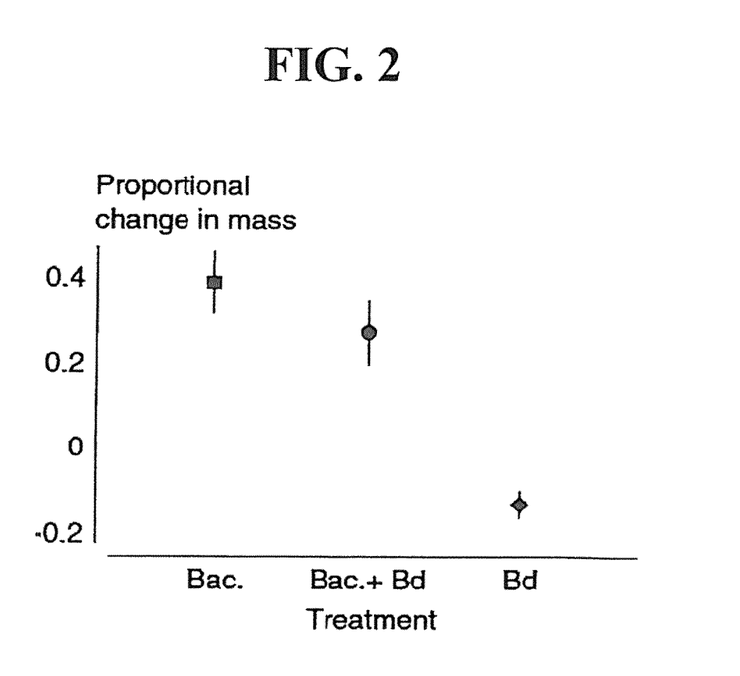

Referring to FIG. 2, frogs in the Bd treatment did not grow and lost some weight on average (FIG. 1*b*). Frogs that were inoculated with *Janthinobacterium lividum* or that were inoculated with *Janthinobacterium lividum* before exposure to Bd grew and gained about 33% of body mass (ANOVA: d.f=2.15, F=17.71, P=0.0001). Frogs in these later two treatments had a daily growth rate that was the same as the growth rate of 10 unmanipulated frogs in a preliminary experiment (see Materials and processes, ANOVA: d.f.=2.19, F=0.81, P=0.461), suggesting that bacteria addition alone did not affect growth rate and that bacterial addition before exposure to Bd prevented weight loss that was associated with Bd infection.

d. Bd Abundance Embodiment

Figure 3:
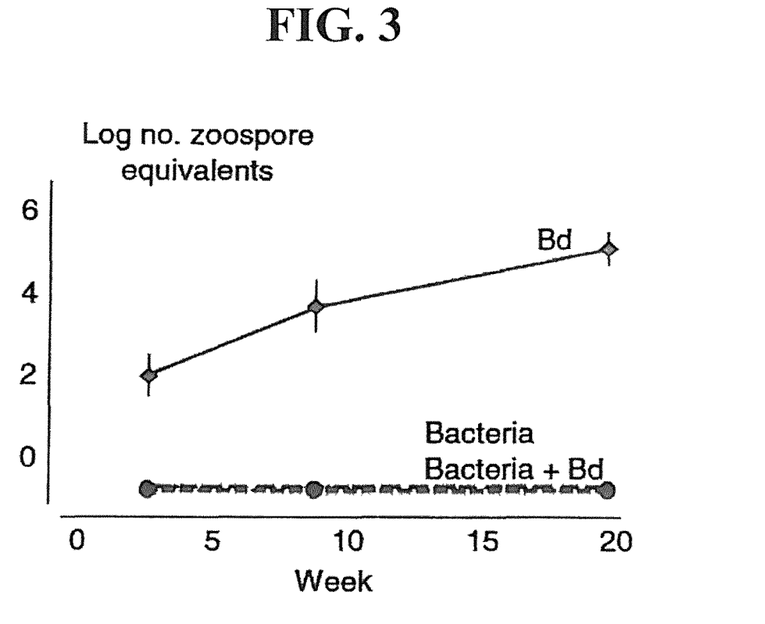

The number of zoospore equivalents measured by qPCR is an index of Bd abundance. Referring to example FIG. 3, zoospore equivalents on frogs in the Bd treatment increased exponentially as the experiment progressed. Frogs in the Bacteria and the Bacteria+Bd treatments had no detectable zoospore equivalents on their skins from the day of the first sample (day 19) until our last sample (day 139), which was a dramatic difference from the Bd treatment (repeated measures ANOVA for the treatment×time interaction: d.f.=4.28, Wilks' λ=0.179, P=0.0001). Furthermore, the bacteria added to frog skins in the Bacteria+Bd treatment prevented successful establishment by Bd zoospores (Kruskal-Wallis test-day 19: d.f.=2, X2=12.645, P=0.013; day 62: d.f.=2, X2=16.129, P=0.0003 and day 139: d.f.=2, $X^2$=16.129, P=0.0003).

e. Violacein Embodiment

Figure 4:
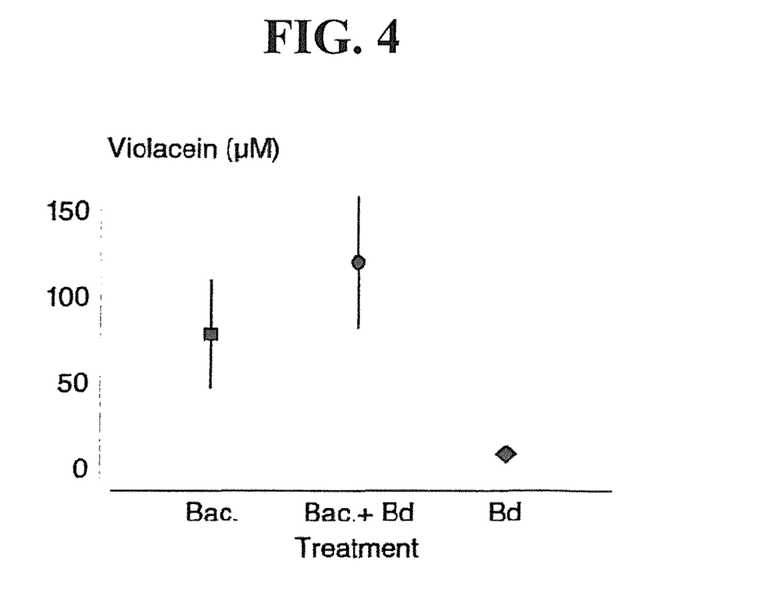

Referring to example FIG. 4, survival of frogs was strongly associated with presence of violacein, an anti-Bd metabolite produced by *Janthinobacterium lividum*. The five frogs that died in the Bd treatment had no detectable violacein concentration on their skin. The frog that survived in the Bd treatment did not have detectable quantities of violacein (<5 μM); however, its weight loss, zoospore load and lethargic behavior indicated serious Bd infection. The mean violacein concentrations were much higher on frog skins in the Bacteria and the Bacteriapd treatments than in the Bd treatment (Kruskal-Wallis test: d.f.=2, X2=8.727, P=0.018). The three juveniles that were not exposed to *Janthinobacterium lividum* or Bd had no detectable violacein concentration on their skins.

B. *Janthinobacterium Lividum* Over Human Host And/Or Host Area(S) Embodiment

1. Materials And Processes Embodiment

According to embodiments, athlete's foot samples may be obtained and grown on Sabouraud's dextrose agar. In embodiments, macroscopic and/or microscopic analysis may be performed to confirm samples included *T. rubrum*. DNA extraction, PCR, and Blast analysis may be employed to further confirm that isolates included *T. rubrum*.

According to embodiments, samples may be tested on three 1% tryptone plates. Two of the plates were for the experimental treatments; one was for the control treatment. All 1% tryptone plates were separated into four equal quadrants using a marker on the outside of the Petri dishes. For the experimental treatments, isolated *Janthinobacterium lividum* was spread vertically and horizontally on the Petri dish along the lines of the marker using a sterile toothpick. Sterile toothpicks were used to place a single spot of the Athlete's foot fungus in each quadrant. The spot was placed approximately 2 mm from the vertical and horizontal dividing lines. The control plates were treated in substantially the same manner except they did not have any *Janthinobacterium lividum* spread. A sterile toothpick was spread along the line *Janthinobacterium lividum* would have been spread as a further level of control. A single Petri dish was prepared using only *Janthinobacterium lividum* to ensure that it was viable.

According to embodiments, the shortest linear distance between the Athlete's foot colony and the vertical and horizontal *Janthinobacterium lividum* lines were measured and averaged for each quadrant at days nine and fourteen. Additionally, the shortest linear distance between the Athlete's foot colony and the horizontal and vertical dividing lines for each quadrant were measured nine and fourteen days into the experiment. Pictures of all experiments were taken three, seven, nine, and fourteen days into the experiment. Treatment one grew as a lawn and was only recorded via pictures.

2. Results Embodiment

*Janthinobacterium lividum* can minimize Athlete's foot fungus, *Tricophyton rubrum*, at least in vitro on dual culture challenge assays. *T. rubrum* colonies grew substantially smaller when in the presence of *Janthinobacterium lividum*. Treatment 1 did not form distinct colonies so it was not possible to measure linear distances between the fungus and *Janthinobacterium lividum* or the dividing lines. However, *T. rubrum* grew much more strongly furthest away from the *Janthinobacterium lividum*.

Figure 5:
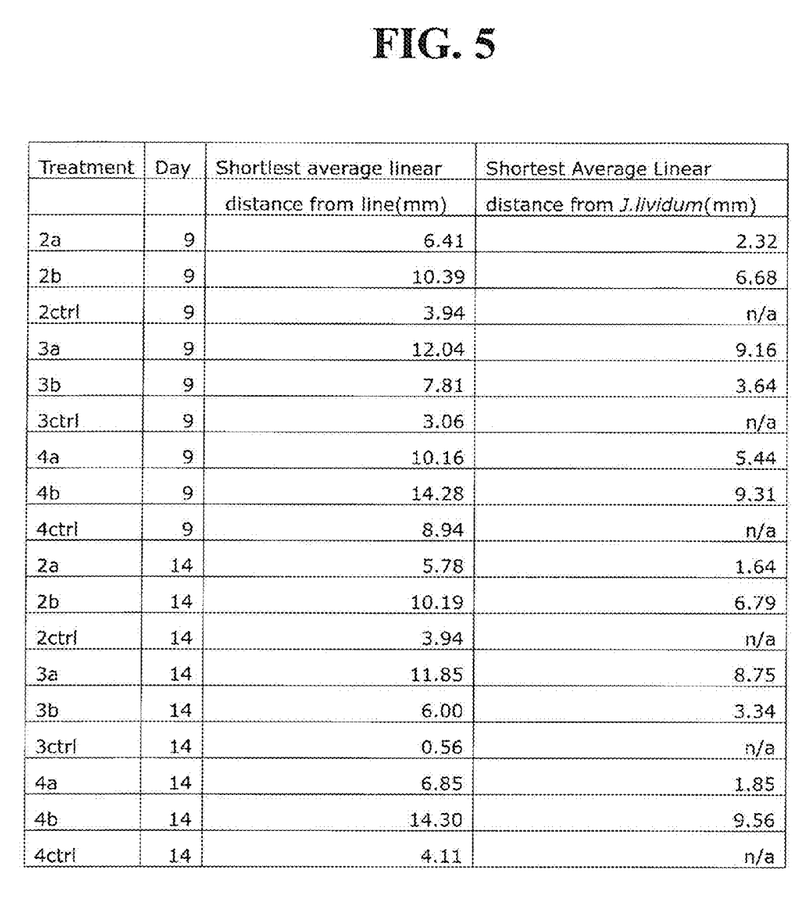
Figure 6:
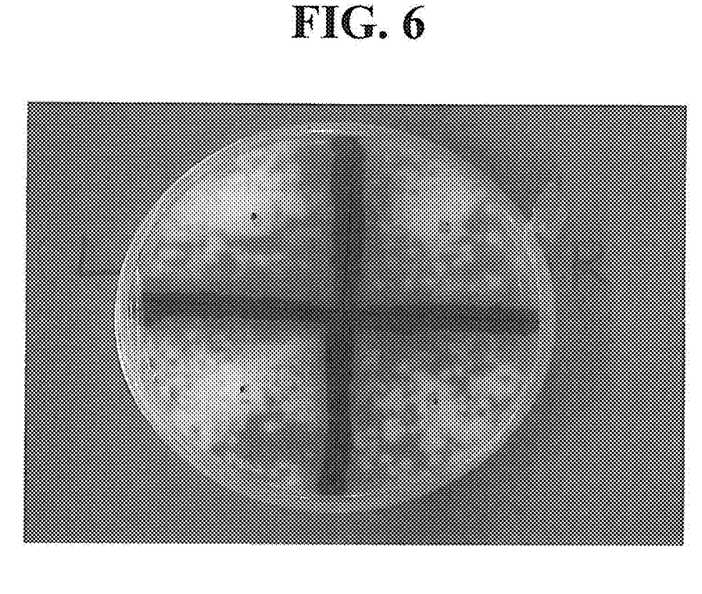

Referring to example FIG. 5, *T. rubrum* colonies grew smaller when in the presence of *Janthinobacterium lividum*. Measurements were not taken for treatment 1 because circular colonies did not form. However, referring to example FIG. 6, a distinct, gradient away from the *Janthinobacterium livi-*

Figure 7:
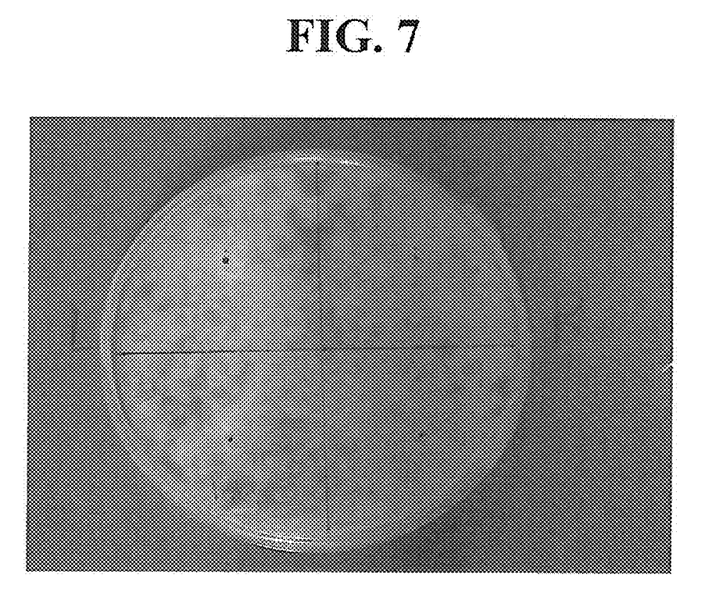

*dum* was observed. Referring to example FIG. 7, *T. rubrum* grew over substantially the entire surface of the plate in the control for treatment 1, designated 1cntrl (i.e., first experiment control treatment with no *Janthinobacterium lividum* present).

Figure 8:
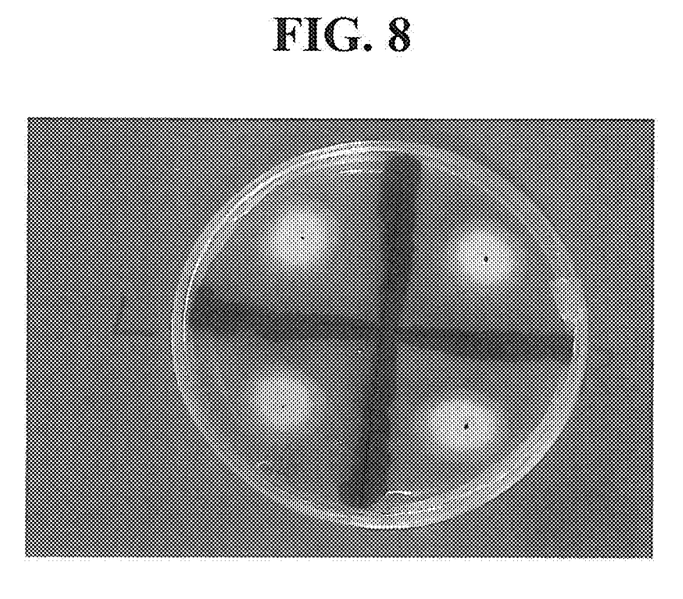
Figure 9:
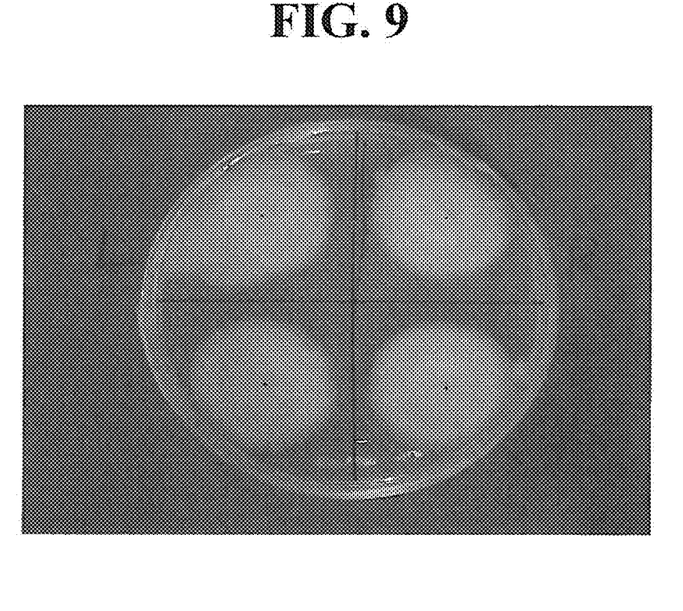

Referring to FIG. 8, treatment 2b taken fourteen days into the dual culture challenge assay is illustrated in accordance with embodiments. This is the second replicate of the dual culture challenge assay of *Janthinobacterium lividum* and *T. rubrum*. *T. rubrum* has formed relatively smaller colonies when compared to the control treatment, for example as illustrated in example FIG. 9. Referring to FIG. 9, treatment 2ctrl taken fourteen days into the dual culture assay is illustrated in accordance with embodiments. This is the control treatment with no *Janthinobacterium lividum* present. *T. rubrum* has formed very large circular colonies when compared to 2b, for example FIG. 8.

Figure 10:
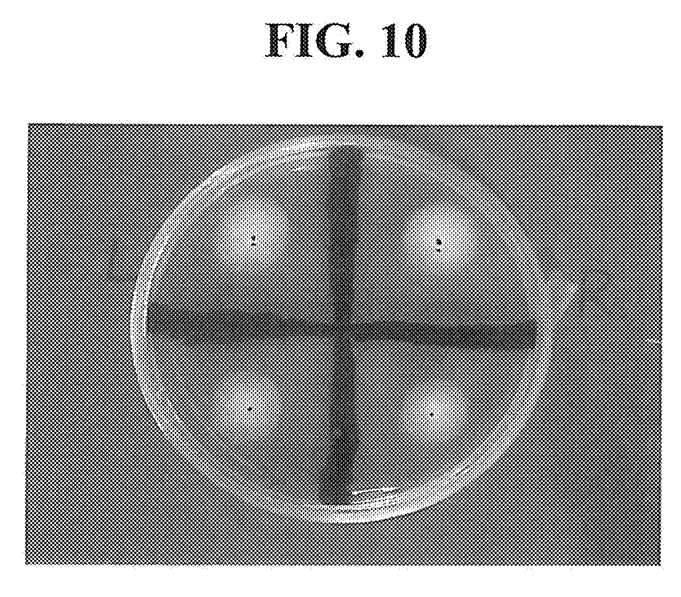
Figure 11:
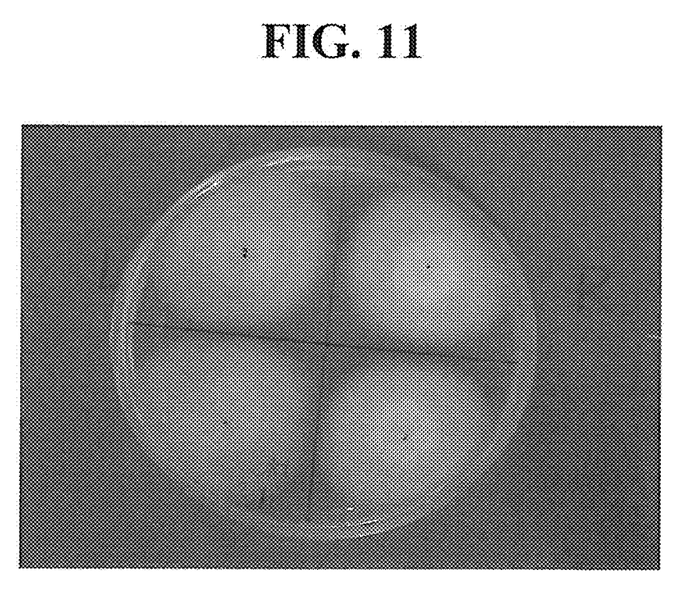

Referring to FIG. 10, treatment 3a taken fourteen days into the dual culture assay is illustrated in accordance with embodiments. This is the first replicate of the dual culture challenge assay of *Janthinobacterium lividum* and *T. rubrum*. *T. rubrum* has formed relatively smaller colonies compared to 3ctrl, for example FIG. 11. Referring to FIG. 11, treatment 3ctrl taken fourteen days into the dual culture assay is illustrated in accordance with embodiments. This is the control treatment with no *Janthinobacterium lividum* present. *T. rubrum* has formed extremely large circular colonies when compared to 3a, for example FIG. 10.

Figure 12:
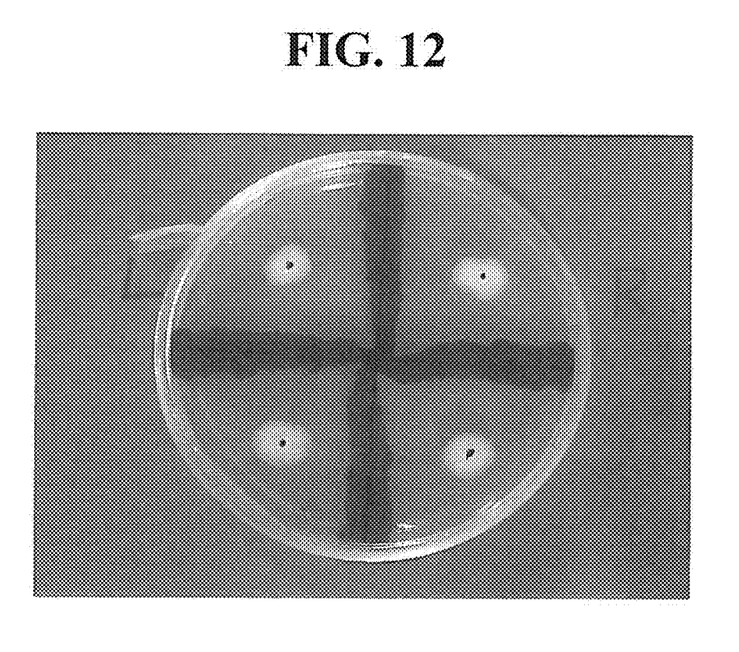
Figure 13:
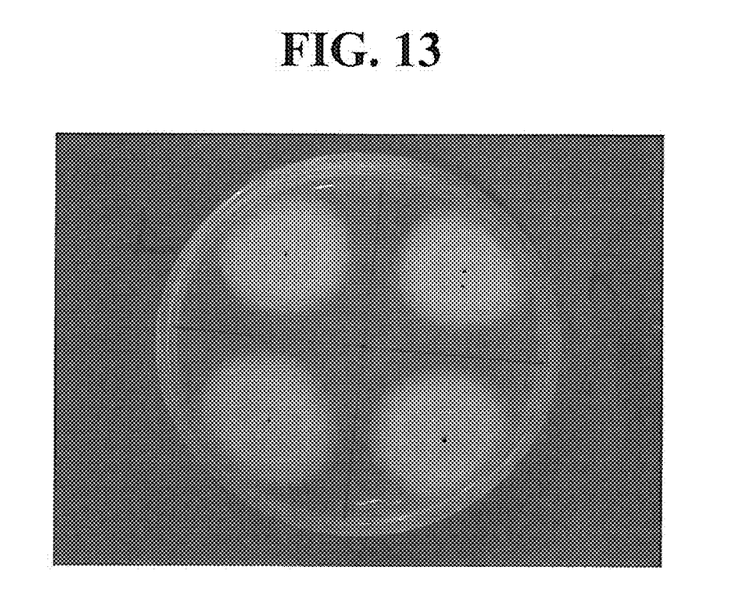

Referring to FIG. 12, treatment 4b taken fourteen days into the dual culture assay is illustrated in accordance with embodiments. This is the second replicate of the dual culture challenge assay of *Janthinobacterium lividum* and *T. rubrum*. *T. rubrum* has formed relatively smaller colonies compared to 4ctrl, for example FIG. 13. Referring to FIG. 13, treatment 4ctrl taken fourteen days into the dual culture assay is illustrated in accordance with embodiments. This is the control treatment with no *Janthinobacterium lividum* present. *T. rubrum* has formed extremely large circular colonies when compared to 4b, for example FIG. 12.

C. Maximizing *Janthinobacterium Lividum* Metabolite Embodiment

1. Materials And Processes Embodiment

According to embodiments, L-Tryptophan (L-Tryp), an amino acid, may increase violet pigmentation of *Janthinobacterium lividum*. The antifungal metabolite violacein ($C_{20}H_{13}N_3O_3$) may be manufactured by *Janthinobacterium lividum* and gives the bacteria its purple coloration. Experiments were performed to test the effect of varying L-Tryptophan concentrations on violacein production. Eight culture flasks were inoculated with isolated *Janthinobacterium lividum* and 0, 0, 2.458, 2.453, 5.127, 5.435, 9.749, and 9.93 mM of L-Tryp were added to each, respectively. Observations were recorded over a seven day period for biofilm pigment intensity and thickness. After seven days, the metabolites were centrifuged and extracted with 1-butanol, then run on a reverse phase high performance liquid chromatography (RP-HPLC). Samples around 11.3 minutes and 575 nm were collected.

2. Results Embodiment

Figure 14:
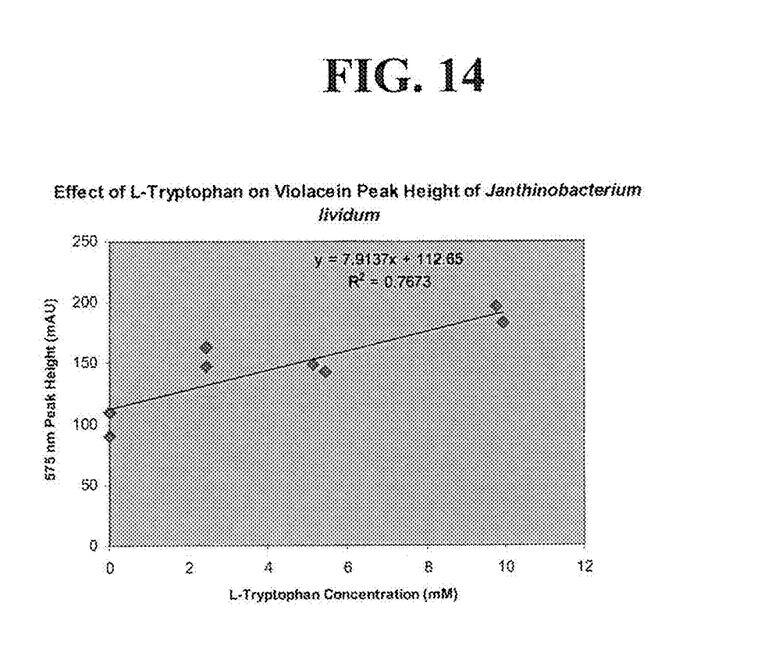

According to embodiments, L-Tryptophan, an amino acid, may increase violet pigmentation of *Janthinobacterium lividum*. Referring to FIG. 14, a graph illustrates an increase of violacein peak height (mAU) as L-Tryp concentrations increase in accordance with embodiments. A regression analysis was completed and a p-value of 8.61442E-05 was established (p-value<0.05). The p-value indicates a statistically positive correlation between added L-Tryptophan and violacein peak height. The correlation coefficient was r=0.8760.

Figure 15:
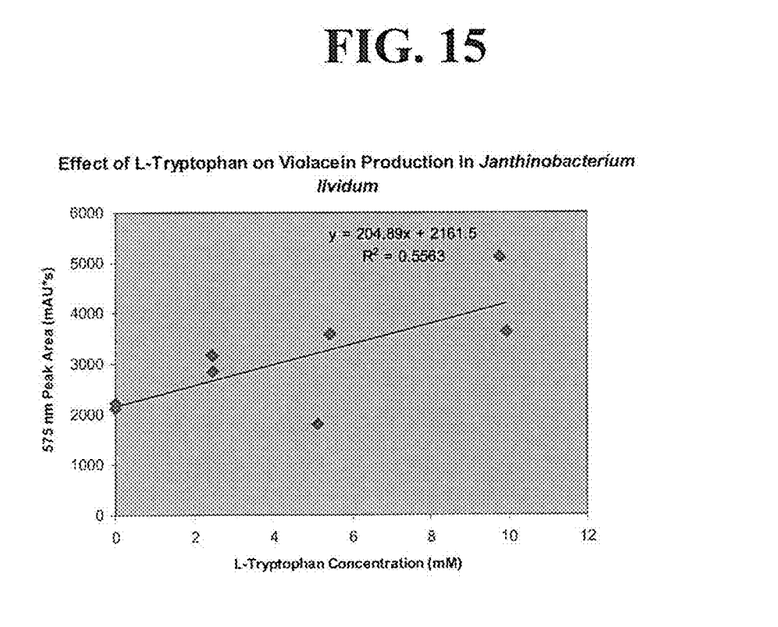

Referring to FIG. 15, a graph illustrates an increase in violacein concentration (mAU*s) as L-Tryp concentrations increases in accordance with embodiments. A regression analysis was completed and a p-value of 4.4443E-06 was established (p-value<0.05). The p-value indicates a statistically positive correlation between added L-Tryptophan and violacein peak area. The correlation coefficient was r=0.7459.

It will be obvious and apparent to those skilled in the art that various modifications and variations can be made in the embodiments disclosed. Thus, it is intended that the disclosed embodiments cover the obvious and apparent modifications and variations, provided that they are within the scope of the appended claims and their equivalents.

What is claimed is:

1. A process to minimize a microbe colony growth comprising applying to human skin a composition including isolated *Janthinobacterium lividum* and a pharmaceutically acceptable carrier.

2. The process of claim 1, wherein the skin is human foot skin.

3. The process of claim 1, wherein said microbe comprises at least one of bacteria, yeast, fungus and virus.

4. The process of claim 3, wherein said fungus comprises *Tricophyton rubrum*.

5. The process of claim 1, wherein said *Janthinobacterium lividum* produces violacein up to approximately 29° C.

6. The process of claim 1, wherein said *Janthinobacterium lividum* comprises between approximately $25 \times 10^6$ and $6.4 \times 10^7$ cells per ml of said pharmaceutically acceptable carrier.

7. The process of claim 6, wherein said *Janthinobacterium lividum* produces between approximately 18 µM and 129 µM of violacein.

8. The process of claim 1, wherein said pharmaceutically acceptable carrier comprises at least one of an emulsion, paste, cream, lotion, gel, jelly, ointment, oil, aerosol, powder and solvent.

9. The process of claim 1, wherein said composition comprises a stimulant to maximize at least violacein.

10. The process of claim 9, wherein said stimulant comprises tryptophan.

11. The process of claim 1, comprising applying a sanitizer to said skin prior to applying said composition.

12. The process of claim 11, wherein said sanitizer comprises hydrogen peroxide.

13. The process of claim 1, wherein said *Janthinobacterium lividum* is in a lysed form.

14. A process to minimize *Tricophyton rubrum* colony growth comprising applying to skin a composition including isolated *Janthinobacterium lividum* and a pharmaceutically acceptable carrier.

15. A process to minimize a microbe colony growth comprising applying to skin a composition including isolated *Janthinobacterium lividum*, a stimulant to maximize at least violacein, and a pharmaceutically acceptable carrier.

16. A process to minimize a microbe colony growth comprising applying to skin a composition including isolated

*Janthinobacterium lividum* and a pharmaceutically acceptable carrier, wherein said *Janthinobacterium lividum* is in a lysed form.

\* \* \* \* \*

UNITED STATES PATENT AND TRADEMARK OFFICE
CERTIFICATE OF CORRECTION

PATENT NO. : 8,506,952 B2
APPLICATION NO. : 12/829520
DATED : August 13, 2013
INVENTOR(S) : Kevin P. C. Minbiole and Reid Harris It is certified that error appears in the above-identified patent and that said Letters Patent is hereby corrected as shown below:

In the Specification

Replace the second paragraph at Column 1, Line 8 with the following:
This invention was made with government support under 0640373 awarded by the National Science Foundation. The government has certain rights in the invention.

Signed and Sealed this
Twenty-seventh Day of June, 2023

Katherine Kelly Vidal
*Director of the United States Patent and Trademark Office*